United States Patent [19]

Berger et al.

[11] 4,069,330
[45] Jan. 17, 1978

[54] NITROPYRAZOLE COMPOUNDS AND ANTI-MICROBIAL COMPOSITIONS

[75] Inventors: Herbert Berger, Mannheim-Kafertal; Rudi Gall, Hirschberg-Grossachsen; Max Thiel, Mannheim; Wolfgang Schaumann, Heidelberg; Wolfgang Vömel, Mannheim, all of Germany

[73] Assignee: Boehringer Mannheim GmbH, Mannheim, Germany

[21] Appl. No.: 678,588

[22] Filed: Apr. 20, 1976

[30] Foreign Application Priority Data

May 22, 1975 Germany .............................. 2522688

[51] Int. Cl.$^2$ .................. A61K 31/415; C07D 231/16
[52] U.S. Cl. .................................. 424/267; 260/293.7; 424/248.54; 424/273 P; 544/140; 548/377; 548/374
[58] Field of Search ............ 260/310 R, 293.7; 424/273, 267

[56] References Cited

U.S. PATENT DOCUMENTS 3,875,182   4/1975   Bretchneider .................. 260/310 R

OTHER PUBLICATIONS

Gardner et al., Chemical Abstracts, vol. 78, 4247u, 1973.

*Primary Examiner*—Natalie Trousof
*Assistant Examiner*—Jane T. Fan
*Attorney, Agent, or Firm*—Burgess, Dinklage & Sprung

[57] ABSTRACT

New nitropyrazole compounds of the formula

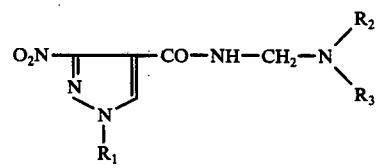

wherein
$R_1$ is alkyl or hydroxyalkyl
$R_2$ and $R_3$, which may be the same or different, are alkyl or
$R_2$ and $R_3$ together represent a 4- or 5-membered alkylene bridge which is optionally interrupted by an oxygen atom or by the grouping $>$N-R, in which R is an alkyl or hydroxyalkyl radical;

and the pharmacologically compatible salts thereof, possess excellent anti-microbial action not only in vitro but also in vivo, especially systemically.

13 Claims, No Drawings

NITROPYRAZOLE COMPOUNDS AND ANTI-MICROBIAL COMPOSITIONS

The present invention is concerned with new 3-nitropyrazole compounds and with therapeutic compositions and methods containing and utilizing such compounds.

The new nitropyrazole derivatives according to the present invention are of the formula:

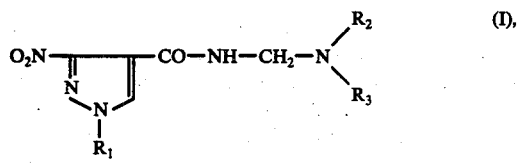

wherein
$R_1$ is alkyl or hydroxyalkyl
$R_2$ and $R_3$, which may be the same or different, are alkyl or
$R_2$ and $R_3$ together represent a 4- or 5-membered alkylene bridge which is optionally interrupted by an oxygen atom or by the grouping >N—R, in which R is an alkyl or hydroxyalkyl radical;
and the pharmacologically compatible salts thereof.

We have found that the new compounds of general formula (I) possess an excellent anti-microbial action, not only in vitro but also in vivo, especially systemically.

The alkyl radical substituents in general formula (I) can be straight or branched chained and contain up to 5 and preferably up to 3 carbon atoms.

The new compounds according to the present invention can be prepared by reacting a compound of the general formula:

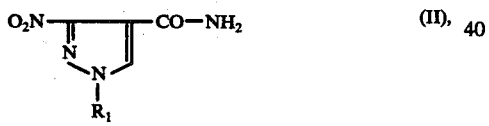

wherein $R_1$ has the same meaning as above, with an amine of the general formula $$R_2—NH—R_3 \quad (III),$$

wherein $R_2$ and $R_3$ have the same meanings as above, in the presence of formaldehyde, whereafter the compound obtained is, if desired, converted into a pharmacologically compatible salt.

The reaction of the compounds of general formula (II) with the compounds of general formula (III) can be carried out in the usual manner in an aqueous medium, preferably in the presence of a water-miscible organic solvent, for example methanol, at an elevated temperature.

The pharmacologically compatible salts can be prepared, for example, by the neutralization of the basic amino group of the compounds (I) with non-toxic inorganic or organic acids. For this purpose, there can be used, for example, hydrochloric acid, sulfuric acid, phosphoric acid, hydrobromic acid, acetic acid, lactic acid, citric acid, oxalic acid, malic acid, salicylic acid, malonic acid, maleic acid, succinic acid or alkyl-sulfonic acids.

The compounds (I) can be administered orally or parenterally in liquid or solid form. Consequently, the present invention also provides pharmaceutical compositions comprising at least one of the new compounds, in admixture with a solid or liquid pharmaceutical diluent or carrier. As injection medium, it is preferable to use water which contains the stabilizing agents, solubilizing agents and/or buffers which are conventional in the case of injection solutions. Examples of such additives include, for example, tartrate and borate buffers, ethanol, dimethyl sulfonoxide, complex-forming agents (such as ethylenediamine-tetraacetic acid), high molecular weight polymers (such as polyethylene oxide) for viscosity regulation and polyoxyethylene derivatives of sorbitan anhydrides. Since the new compounds, as Mannich bases, give neutral aqueous solutions with acids, it is also possible to prepare aqeuous injection solutions without the help of solubilizing agents.

Solid carrier materials which can be used include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

Apart from the compounds mentioned in the following Examples, preferred compounds according to the present invention include the following:
1-ethyl-3-nitro-4-pyrazole-N-(pyrrolidinomethyl)-carboxamide;
1-methyl-3-nitro-4-pyrazole-N-(4-β-hydroxyethyl-1-piperazinylmethyl)-carboxamide; and
1-(2-hydroxyethyl)-3-nitro-4-pyrazole-N-(4-methyl-1-piperazinylmethyl)-carboxamide.

The following Examples are given for the purpose of illustrating the present invention:

EXAMPLE 1

Preparation of 1-(2-hydroxyethyl)-3-nitro-4-pyrazole-N-(pyrrolidinomethyl)-carboxamide.

2 g. 1-(2-Hydroxyethyl)-3-nitro-4-pyrazole-carboxamide were stirred with 7.5 ml. methanol, 1.7 ml. pyrrolidine and 1.8 ml. 37% aqueous formaldehyde solution for 4 hours under reflux and then the solution was evaporated in a vacuum. The residue was dissolved in chloroform, dried over anhydrous sodium sulfate, filtered and the filtrate evaporated in a vacuum. The oily residue obtained was left to crystallize for a few days, then triturated with a little isopropanol and left to stand in the cold for 2 days. The crystals obtained were filtered off with suction, washed with a little isopropanol and ether and dried in a vacuum at 60° C. There was obtained 1.8 g. 1-(2-hydroxyethyl)-3-nitro-4-pyrazole-N-(pyrrolidinomethyl)-carboxamide in the form of a bright yellow product; m.p. 104°–106° C.

EXAMPLE 2

Preparation of 1-methyl-3-nitro-4-pyrazole-N-(piperidinomethyl)-carboxamide.

1.7 g. 1-Methyl-3-nitro-4-pyrazole-carboxamide was stirred with 0.85 g. (1ml.) piperidine, 6 ml. methanol and 0.75 ml. 37% aqueous formaldehyde solution for 2.5 hours under reflux. 0.3 ml. Piperidine was then added thereto and stirring continued for 1.5 hours under reflux. A further 0.7 ml. piperidine and 0.75 ml. 37% aqueous formaldehyde solution were added, stirring was continued for 4 hours under reflux and the reaction mixture was then evaporated to dryness in a vacuum. The residue wastriturated with water and dried in a vacuum, first at ambient temperature and then at 80° C. There was obtained 1.99 g. 1-methyl-3-nitro-4-pyrazole-N-(piperidinomethyl)-carboxamide in the form of a white product; m.p. 142°-144° C.

EXAMPLE 3

Preparation of
1-methyl-3-nitro-4-pyrazole-N-(pyrrolidinomethyl)-carboxamide.

1 g. 1-Methyl-3-nitro-4-pyrazole-carboxamide was stirred with 35 ml. methanol, 1 ml. pyrrolidine and 0.9 ml. 37% aqueous formaldehyde solution for 4 hours under reflux and then the solution was evaporated in a vacuum. The residue was triturated with water, filtered off with suction, washed with water and dried in a vacuum at 80° C. There was obtained 1.12 g. 1-methyl-3-nitro-4-pyrazole-N-(pyrrolidinomethyl)-carboxamide in the form of a white product; m.p. 127°-130° C.

A sample of the compound, suspended in water, goes into solution after the addition of acetic acid up to a pH value of about 5-6 and, after the addition of 2N aqueous sodium hydroxide solution, again crystallizes out.

EXAMPLE 4

Preparation of
1-methyl-3-nitro-4-pyrazole-N-(diethylaminomethyl)-carboxamide.

1 g. 1-Methyl-3-nitro-4-pyrazole-carboxamide was stirred with 3.5 ml. methanol, 1.21 ml. diethylamine and 0.9 ml. 37% aqueous formaldehyde solution for 4 hours under reflux. A further 0.4 ml. diethylamine and 0.3 ml. formaldehyde solution were added thereto and the reaction mixture was stirred for a further 2 hours under reflux and then evaporated to dryness in a vacuum. The residue was dissolved in chloroform, dried over anhydrous sodium sulfate and filtered and the filtrate was evaporated. The evaporation residue (1.3 g.) was triturated with diisopropyl ether and the crystals obtained are dried in a vacuum at ambient temperature. There was thus obtained 0.96 g. 1-methyl-3-nitro-4-pyrazole-N-(diethylaminomethyl)-carboxamide; m.p. 69°-71° C. (changes from 65° C.).

In an analogous manner, from 1-methyl-3-nitro-4-pyrazole-carboxamide, morpholine and 37% aqueous formaldehyde solution, there was obtained 1-methyl-3-nitro-4-pyrazole-N-(morpholinomethyl)-carboxamide; m.p. 128°-129° C. (changes from 123° C.).

As noted above, the new 3-nitropyrazole compounds possess outstanding in vitro and in vivo antimicrobial action, against bacteria and Protozoa, such as Trichomonades and Salmonellae, which may be present in the digestive or other systems of mammals. This utility is, of course, shared by the pharmacologically acceptable salts of the 3-nitropyrazole compounds, which salts are conventional in the art.

The antimicrobial activity of the instantly disclosed compounds was confirmed by the testing of a number of representative or illustrative compounds in certain tests. The following were the test compounds of the invention:

Compound I - 1-(2-Hydroxyethyl)-3-nitro-4-pyrazole-N-(pyrrolidinomethyl)-carboxamide.
Compound II - 1-Methyl-3-nitro-4-pyrazole-N-(piperidinomethyl)-carboxamide.
Compound III - 1-Methyl-3-nitro-4-pyrazole-N-(pyrrolidinomethyl)-carboxamide.
Compound IV - 1-Methyl-3-nitro-4-pyrazole-N-(morpholinomethyl)-carboxamide.
Compound V - 1-Methyl-3-nitro-4-pyrazole-N-(diethylaminomethyl)-carboxamide.

In one series of tests, the bacteriostatic activity of certain illustrative compounds of this invention in urine was tested and the percentage of administered test substance excreted in the urine was determined, after oral administration, in rats. The comparison substance "Furadantin" (nitrofurantoine) was used in side-by-side comparisons. The results obtained are set forth in Table 1 below, in which the column headed "Maximal Dilution" represents the maximum extent to which a urine sample could be diluted and still exhibit bacteriostatic activity against the test bacterium, which was Escherichia Coli (106). The test compounds were administered at the rate 80 mg of test compound per kg of the rat's body weight, and are on the basis of 75 ml of urine taken 22 hours after oral administration of the test compound. Each test value is based on the averages of values obtained in tests in nine rats and in the instances where two values are set forth, two determinations were made. The corresponding value for the reference standard "Furadantin" are set forth at the bottom of Table 1. It can be seen that the compounds representative of the instant invention were capable of being diluted to a substantially greater extend than Furadantin, and still exhibit bacteriostatic activity; also, most of the compounds of the invention were excreted in urine to a much greater extent than Furadantin.

TABLE 1

| Bacteriostatic Activity in Urine in Rats After Oral Administration | |
|---|---|
| Test Substance | Maximal Dilution |
| Compound I | 1:493 |
| Compound II | 1:47 |
| Compound III | 1:30 |
| Compound IV | 1:43 |
| Nitrofurantoine ("Furadantin") | 1:19 |
| | 1:21 |

In another series of tests, the in vivo effectiveness of the inventive compounds in mice was determined, according to the following procedure.

Female mice (inbreeding strain NMRI), weight 19-21 g, infected by injecting 0.5 ml of a diluted 18-hour bouillon culture of Escherichia Coli (108) intraperitoneally into the animals. The intensity of the infection was adjusted so that without treatment at least 95% of the animals died during the first two days. 40 animals were used for these infection controls.

Treatment:

The treatment took place directly after the infection in form of a single subcutaneous dose. The volume of the single dosage amounted ot 0.5 ml (substance dissolved in distilled water or 5% tylose mucus). 10 animals were used in each test at each dosage.

In each case, ten control animals were not infected but only treated with the two highest dosages of the test substances. These control tests served as a basis for determining the losses of animals caused by the test compound.

The animals were observed for ten days. The number of the deceased animals was determined daily.

The results are set forth in Table 2, below.

TABLE 2

| | In Vivo Tests in Mice | | |
|---|---|---|---|
| | % Surviving animals | | |
| Test Compound | 320 mg/kg subcutaneously | 160 mg/kg subcutaneously | 80 mg/kg subcutaneously |
| Compound II | 100 | 100 | 100 |
| Compound III | 100 | 100 | 100 |
| Compound V | 100 | 100 | 90 |
| Comparison Substance | | | |
| Penicillin G | 100 | 90 | 40 |

The compounds of general formula (I) and the salts thereof can be administered orally and parenterally in liquid or solid form. As injection medium, it is preferred to use water which contains the stabilizing agents, solubilizing agents and/or buffers conventional for injection solutions. Additions of this type include, for example, tartrate and borate buffers, ethanol, dimethylsulfoxide, complex-forming agents (such as ethylenediamine-tetraacetic acid), high molecular weight polymers (such as liquid polyethylene oxide) for viscosity regulation and polyoxyethylene derivatives of sorbitol anhydrides.

Examples of solid carrier materials which can be used include starch, lactose, mannitol, methyl-cellulose, talc, highly-dispersed silicic acid, high molecular fatty acids (such as stearic acid), gelatine, agar-agar, calcium phosphate, magnesium stearate, animal and vegetable fats and solid high molecular weight polymers (such as polyethylene glycoles). Compositions suitable for oral administration can, if desired, contain flavoring and/or sweetening agents. For topical application, the new compounds (I) and the salts thereof can be used in the form of powders and salves; for this purpose, they are mixed with, for example, powdered, physiologically compatbile diluents or with conventional salve bases.

The particular mode of administration and dosage of inventive compound to be applied in treating a given bacterial infection or infirmity will, of course, be determined by the physician, taking into account all the circumstances of a particular case. However, in general, tablets containing the test compound to be administered per os, will contain about 250 mg of active material and, for local administration, may contain about 500 mg of active substance. The dosage to be applied may be one tablet taken in the morning and in the evening with the corresponding meal, for, e.g. ten consecutive days, if the compound is applied per os. For local administration, one ovule may be applied for 10 to 20 days every evening. In men, the per os administration may have to be increased to, e.g., 750 mg to 1 g, instead of the standard 250 mg per tablet dosage.

It will be understood that the specification and examples are illustrative but not limitative of the present invention and that other embodiments within the spirit and scope of the invention will suggest themselves to those skilled in the art.

What is claimed is:
1. Nitropyrazole compound of the formula

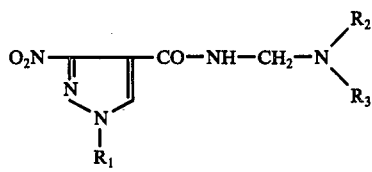

wherein
$R_1$ is alkyl or hydroxyalkyl of up to five carbon atoms
$R_2$ and $R_3$, which may be the same or different, are alkyl of up to five carbon atoms or
$R_2$ and $R_3$ together represent a 4- or 5-membered alkylene bridge,
and the pharmacologically compatible salts thereof.

2. Nitropyrazole compound as claimed in claim 1 wherein $R_1$ is alkyl of up to 5 carbon atoms.

3. Nitropyrazole compound as claimed in claim 1 wherein $R_1$ is hydroxyalkyl of up to 5 carbon atoms.

4. Nitropyrazole compound as claimed in claim 1 wherein $R_2$ and $R_3$ individually are alkyl of up to 5 carbon atoms.

5. Nitropyrazole compound as claimed in claim 1 wherein $R_2$ and $R_3$ taken together represent a 4 to 5 carbon alkylene bridge.

6. Nitropyrazole compound as claimed in claim 1 designated 1-(2-hydroxyethyl)-3-nitro-4-pyrazole-N-(pyrrolidinomethyl)-carboxamide.

7. Nitropyrazole compound as claimed in claim 1 designated 1-methyl-3-nitro-4-pyrazole-N-(piperidinomethyl)-carboxamide.

8. Nitropyrazole compound as claimed in claim 1 designated 1-methyl-3-nitro-4-pyrazole-N-(pyrrolidinomethyl)-carboxamide.

9. Therapeutic compositions having anti-microbial activity comprising a pharmaceutically acceptable carrier and, in anti-microbially effective amounts, a compound as claimed in claim 1.

10. Method of combating microbial infections in subject which method comprises administering to the subject anti-microbially effective amounts of a nitropyrazole compound of the formula

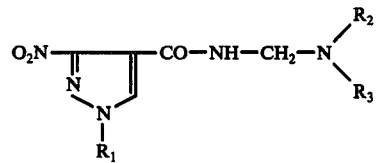

wherein
$R_1$ is alkyl or hydroxyalkyl of up to five carbon atoms
$R_2$ and $R_3$, which may be the same or different, are alkyl of up to five carbon atoms or
$R_2$ and $R_3$ together represent a 4- or 5-membered alkylene bridge,
and the pharmacologically compatible salts thereof.

11. Method as claimed in claim 10 wherein said compound is applied locally.

12. Method as claimed in claim 10 wherein said compound is applied per os.

13. Method as claimed in claim 10 wherein said compound is selected from the group consisting of 1-(2-hydroxyethyl)-3-nitro-4-pyrazole-N-(pyrrolidinomethyl)-carboxamide, 1-methyl-3-nitro-4-pyrazole-N-(piperidinomethyl)-carboxamide, and 1-methyl-3-nitro-4-pyrazole-N-(pyrrolidinomethyl)-carboxamide.

* * * * *

UNITED STATES PATENT OFFICE
CERTIFICATE OF CORRECTION

Patent No. 4,069,330                Dated    January 17, 1978

Inventor(s)   Herbert Berger et al.

It is certified that error appears in the above-identified patent and that said Letters Patent are hereby corrected as shown below:

Title page, "Kafertal" should read -- Käfertal --.

Column 3, line 6, "wastriturated" should read -- was triturated --.

Column 4, line 35, "extend" should read -- extent --.

Column 6, line 35, "compositions" should read -- composition --.

*Signed and Sealed this*

*Twelfth* Day of *December 1978*

[SEAL]

Attest:

RUTH C. MASON
*Attesting Officer*

DONALD W. BANNER
*Commissioner of Patents and Trademarks*